(12) United States Patent
Waugh et al.

(10) Patent No.: US 8,267,310 B2
(45) Date of Patent: Sep. 18, 2012

(54) METHOD AND APPARATUS FOR HANDLING PACKAGES IN AN AUTOMATED DISPENSARY

(76) Inventors: Donald Waugh, Oakville (CA); Richard Panetta, Milton (CA); Peter Suma, Aurora (CA); Leigh Pauls, St. Catherines (CA)

( * ) Notice: Subject to any disclaimer, the term of this patent is extended or adjusted under 35 U.S.C. 154(b) by 145 days.

(21) Appl. No.: 12/701,372

(22) Filed: Feb. 5, 2010

(65) Prior Publication Data

US 2011/0192893 A1   Aug. 11, 2011

(51) Int. Cl.
 *G06F 17/00* (2006.01)
(52) U.S. Cl. ........................................ 235/375; 235/487
(58) Field of Classification Search .................. 235/375, 235/487, 385, 462.01
See application file for complete search history.

(56) References Cited

U.S. PATENT DOCUMENTS

| 5,597,995 | A | 1/1997 | Williams et al. |
|---|---|---|---|
| 5,761,877 | A | 6/1998 | Quandt |
| 6,742,671 | B2 | 6/2004 | Hebron et al. |
| 2003/0034397 | A1* | 2/2003 | Patton ...................... 235/462.14 |
| 2007/0145142 | A1* | 6/2007 | Lubow et al. ............ 235/462.01 |
| 2007/0210164 | A1* | 9/2007 | Conlon et al. ........... 235/462.01 |
| 2009/0173779 | A1* | 7/2009 | Szesko et al. ................. 235/375 |
| 2011/0150346 | A1* | 6/2011 | Panetta ......................... 382/218 |

FOREIGN PATENT DOCUMENTS

WO   WO2008006203 A1   1/2008

* cited by examiner

*Primary Examiner* — Edwyn Labaze
(74) *Attorney, Agent, or Firm* — Bradley K. DeSandro; DeSandro Law Group PLLC

(57) ABSTRACT

In a method and apparatus for handling a package in an automated dispensary, a package is positioned in an inspection station of the dispensary. Images are captured of the package and are read to identify data on labels or on the package itself. The data is encoded as source data in an identifying label which is applied to the package and is used subsequently in handling the package for dispensing and other inventory management procedures.

19 Claims, 6 Drawing Sheets

METHOD AND APPARATUS FOR HANDLING PACKAGES IN AN AUTOMATED DISPENSARY

FIELD OF THE INVENTIO; and,

This invention relates to a method and apparatus for handling packages in an automated dispensary. The invention has particular but not exclusive application to serializing medicament packages in preparation for dispensing from an automated medicament dispensary.

DESCRIPTION OF RELATED ART

The traditional means of dispensing prescribed medicaments involves a doctor meeting with a patient and prescribing a medicament based on a particular diagnosis, and then hand writing and signing a prescription for the patient to carry to a pharmacist at a pharmacy location for fulfillment. In recent years, two significant advances have occurred in the field of medicament dispensing. The first is the advent of electronic prescription capturing methods, systems and apparatus, which improve the overall accuracy and patient record-keeping associated with prescribing medicaments. The second is the advent of automated apparatus, typically configured as dispensaries, from which medicaments can be automatically dispensed, the dispensaries being located for convenient patient access, such as at a doctor's premises, a hospital or mall. In the use of automated dipensaries, the dispensaries are stocked, medicaments are periodically dispensed to patients, and the dispensaries are restocked. For patient safety, it is necessary to verify that valid medicaments are being dispensed to patients. An important step in such verification is serializing all products that are stocked at the dispensary. Serialization is valuable also for effective inventory management. However, serializing products can be time consuming and inconvenient if all products that are to be stocked in a large number of distributed kiosks have to be brought to a central depot for serializing. There is also the risk of loss or damage of products in transporting them to and from the serializing depot. Similarly, to have a person operate dedicated serializing equipment which is either installed at a kiosk or is taken there by a service person can be time consuming and costly.

SUMMARY OF THE INVENTION

According to one aspect of the invention, there is provided a method of handling a package in an automated dispensary, the method comprising positioning the package in an inspection station of the dispensary, capturing an image of the package, reading the image to identify source data, encoding the source data to obtain first encoded data, and labeling the package with an identifying label containing the first encoded data and serializing data. The label can be any suitable label such as a bar code label or a radio frequency identification label.

Preferably the reading of the image further comprises machine reading at least a first part of the image at the inspection station to derive a machine readable part of the source data. The machine reading can further comprise optical character reading printed characters of the image with an OCR reader and/or reading embossed characters of the image with an embossed character reader. Preferably, the dispensary is one node on a communications network, the method further comprising transmitting the image from the dispensary to a remote node, and, at the remote node, manually reading the image to derive a manually viewed part of the source data.

The method can further comprise illuminating the package from several directions and capturing the respective image parts corresponding to the package being viewed from several directions. Optionally, with the package positioned in the inspection station, a physical property of the package is measured to derive physical data, the physical data is encoded to obtain second encoded data, the second encoded data is combined with the first encoded data, and the package is labeled with the identifying label containing the combined data. The method can further comprise illuminating the package with an illuminating module, recording a provisional image of the package with an image capture module prior to capturing a final image of the package by the image capture module, analyzing the provisional image quality, and adjusting settings of at least one of the illuminating module and the image capture module to increase the provisional image quality and obtain the final image.

According to another aspect of the invention, there is provided apparatus for handling a package in an automated dispensary, the apparatus comprising, at an inspection station of the dispensary, an illumination module to illuminate the package, an image capture module for capturing an image of the package, a character identifying module to identify characterizing data from the image, an encoding module to encode the characterizing data, and a labeling module to apply a machine readable label bearing the encoded characterizing data to the package.

Preferably the character identifying module has a reader for reading machine readable characters in the image to derive a machine readable part of the characterizing data, the reader being at least one of a printed character reader and an embossed character reader.

The dispensary can be a node on a communications network, the character identifying module further including a link of the communications network for transmission of the image from the dispensary to a remote node of the communications network, and a manual image inspection unit at the remote node to enable manual inspection of a transmitted image.

The labeling module is preferably operable to apply one of a bar code label and a radio frequency identification label to the package. The illumination module can have multiple light sources to illuminate the package from a plurality of directions, and the image capture module can have multiple image capture camera units to capture images of the package as viewed from a corresponding plurality of directions.

The apparatus can further comprise a physical property measuring module to measure at least one physical property of the package to derive physical data, the encoding module operable to encode the physical data to obtain second encoded data, and the labeling module operable to label the package with a label embodying the second encoded data. The image capture module is preferably operable to capture a provisional image of the package, the reader operable to read the provisional image and to develop a feedback signal, and the apparatus further including a feedback loop to apply the feedback signal to adjust settings of at least one of the illumination module and the image capture module.

BRIEF DESCRIPTION OF THE DRAWINGS

For simplicity and clarity of illustration, elements illustrated in the following figures are not drawn to common scale. For example, the dimensions of some of the elements are exaggerated relative to other elements for clarity. Advantages, features and characteristics of the present invention, as well as methods, operation and functions of related elements of structure, and the combinations of parts and economies of manufacture, will become apparent upon consideration of the following description and claims with reference to the accompanying drawings, all of which form a part of the specification, wherein like reference numerals designate corresponding parts in the various figures, and wherein:

Figure 1:
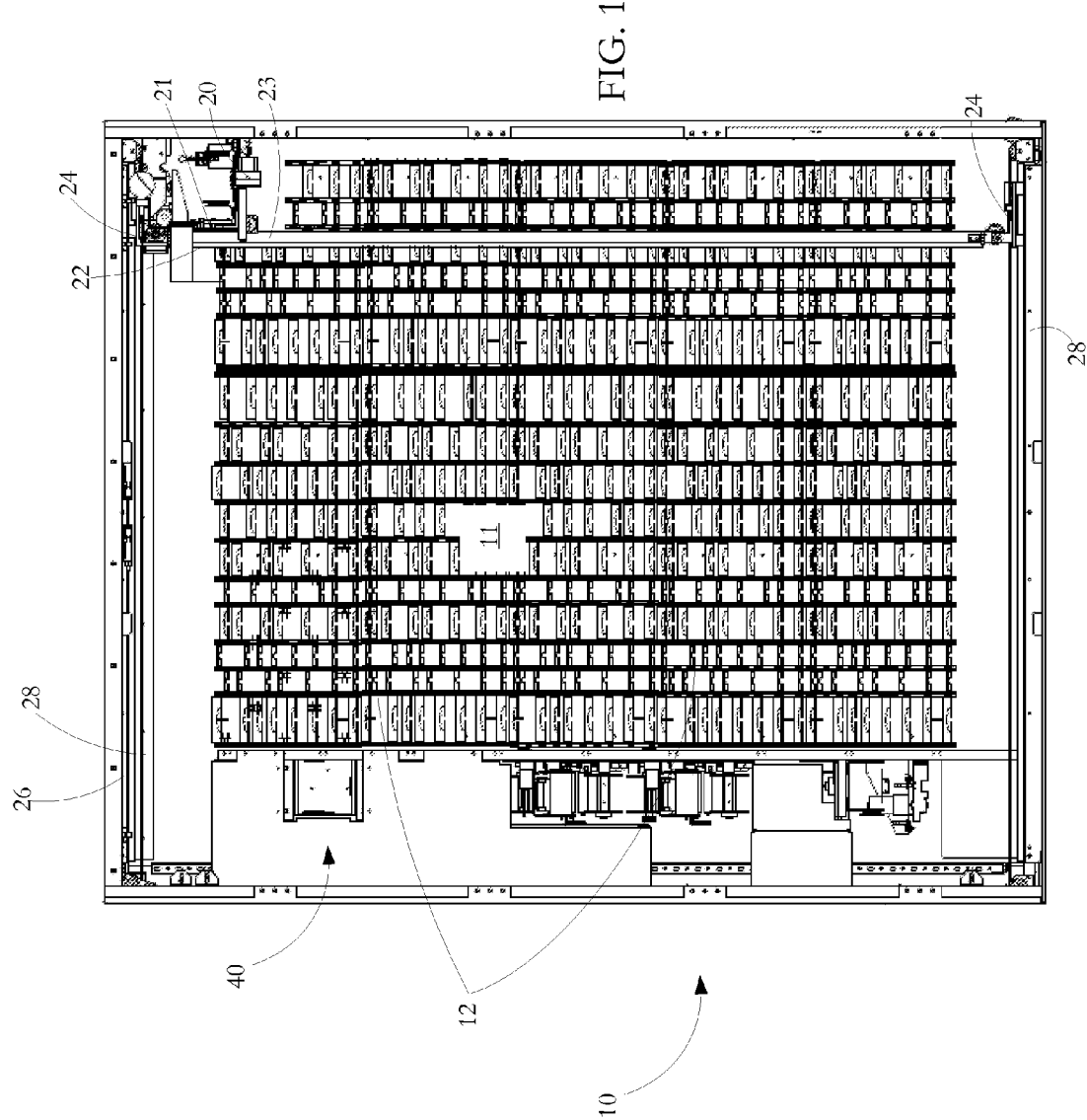
FIG. 1 is front view of a vault of an automated dispensary showing an inspection station.

DETAILED DESCRIPTION OF THE INVENTION INCLUDING THE PRESENTLY PREFERRED EMBODIMENTS

In this specification, the term "medicament" encompasses drugs and any and all other materials dispensed subject to presentation of a prescription or script. The term "station" encompasses bins such as storage and loading bins and other locations within an automated dispensary to which a medicament package is taken and where a package processing activity such as inspection takes place or pending movement of the package to another location. The use of the term "module" in the specification is to distinguish functionally distinct parts of the package handling apparatus, which parts may however comprise mechanical elements, control logic, processing means and memory which are common to or shared by other parts.

Applicant's copending PCT Application Serial No. PCT/CA2007/001220 relates to a method, system and apparatus for dispensing medicaments. More specifically, the PCT application describes a networked system having a server, a database of patient information linked to the server, a first client having input means linked to the server and operable to generate a script for a medicament prescribed to a user, a second client comprising an automated dispensary at which medicaments can be dispensed to a user, the dispensary including an input means operable to recognize a human and/or machine readable description in the script, and to provide validating cross-referencing between the description and patient information as a prelude to dispensing a medicament to the user on the basis of the input script. A doctor in a clinic can be a third client having input means linked to the server to input appropriate prescription information, or accept certain prescription information from the database as being applicable in the particular case for a particular patient. Further, the doctor's client device can be operable to display patient information, e.g., medicament history, insurance coverage, etc., and a printer module can print the script as a paper print-out.

The server and database enable storing, compiling and retrieval of patient data including name, address, and diagnostic and medicament history. Access to the database can be provided to both the doctor and the automated apparatus for dispensing medicaments via the server, via a secure connection, or via a link between the system and a clinic's existing clinic management system or patient database.

The described apparatus may also includes a user interface, a teleconferencing or video-conferencing means enabling communication between the user and a human validation agent, and a scanning means for capturing an image of the script so that it, if needed, it can be viewed by a human validation agent, such as a licensed pharmacist communicating in the system and with the apparatus from a remote location to the apparatus, to approve a prescription. The user interface of the dispensary apparatus provides detailed and clear instructions to guide the user.

An authentication means confirms the identity of the patient, for example, by prompting for a personal identification number or by biometric means or by associating certain questions to answers provided by the patient that identify the patient to the apparatus, and cross-referencing this information with the patient information stored on the networked database. Once the patient is recognized, the dispensary apparatus prompts the user for a script and the apparatus processes the user-input script either by the above-mentioned human validation agent or by processing the machine readable description (which may be a bar code). This information can be verified with the server and the database. The apparatus may also interface with the server to adjudicate insurance claims and to determine amounts payable by patients. The patient either accepts or rejects the transaction. If the transaction is accepted, the apparatus interfaces with the server to transact a payment, for example, by prompting the patient for credit card information. Prescription labels and receipts are printed. The apparatus confirms that the medicament is correct and delivers it to a dispensing area for retrieval by the user while retaining the script in a lock box, and verifying that the purchased medicament product has been retrieved. Further, the apparatus may print and/or provide to the user educational materials relevant to the medicaments that have been dispensed. The automated dispensing apparatus forming one node of a communication network is of significant value in enabling a patient to obtain prescribed medicaments without having to attend a pharmacy or medicament store.

As part of such an automated dispensary, a medicament vault having a rack assembly is described in U.S. patent application Ser. No. 12/541,307 which is hereby incorporated by reference in its entirety. As shown in FIG. 1, such a vault 10 includes a row column rack 11 of bins 12, each of the bins being rectangular in form, although other bin shapes are contemplated. The rack structure permits the spacing of bin side walls and the spacing of bin floors from their tops to be readily altered. By suitable selection of the spacings, a large variety of sizes can be obtained. Medicament packages may have a range of shapes and sizes depending on both the size of the medicament itself and the size of the surrounding packaging. Because space is at a premium, ideally the size of a particular bin 12 should closely match the size of the medicament package housed in that bin. Because the distribution of package size distribution normally varies from dispensary to dispensary, the distribution of bin sizes in a bin rack is tailored for the particular dispensary.

The automated dispensary also includes a package handling apparatus. As shown in FIG. 1, the apparatus includes a gantry on which is mounted a pick head. The gantry includes a vertically reciprocable carriage 21 which is driven by a belt drive 22 along a vertical guide rail 23. The rail 23 is mounted between two linked, horizontally reciprocable carriages 24.

The carriages 24 are driven by a belt drive 26 along horizontal rails 28. The carriages 21 and 24 are movable in an access plane extending parallel to a front side of the bin rack 11. In this way, a pick head 20 can be placed adjacent any selected one of the storage bins 12 or any other functional station forming part of the vault. To pick a package from a bin, a platform forming part of the pick head is moved in a direction perpendicular to the access plane to a position from where a selected package can be withdrawn from a chosen bin or can be placed into a chosen bin.

Figure 2:
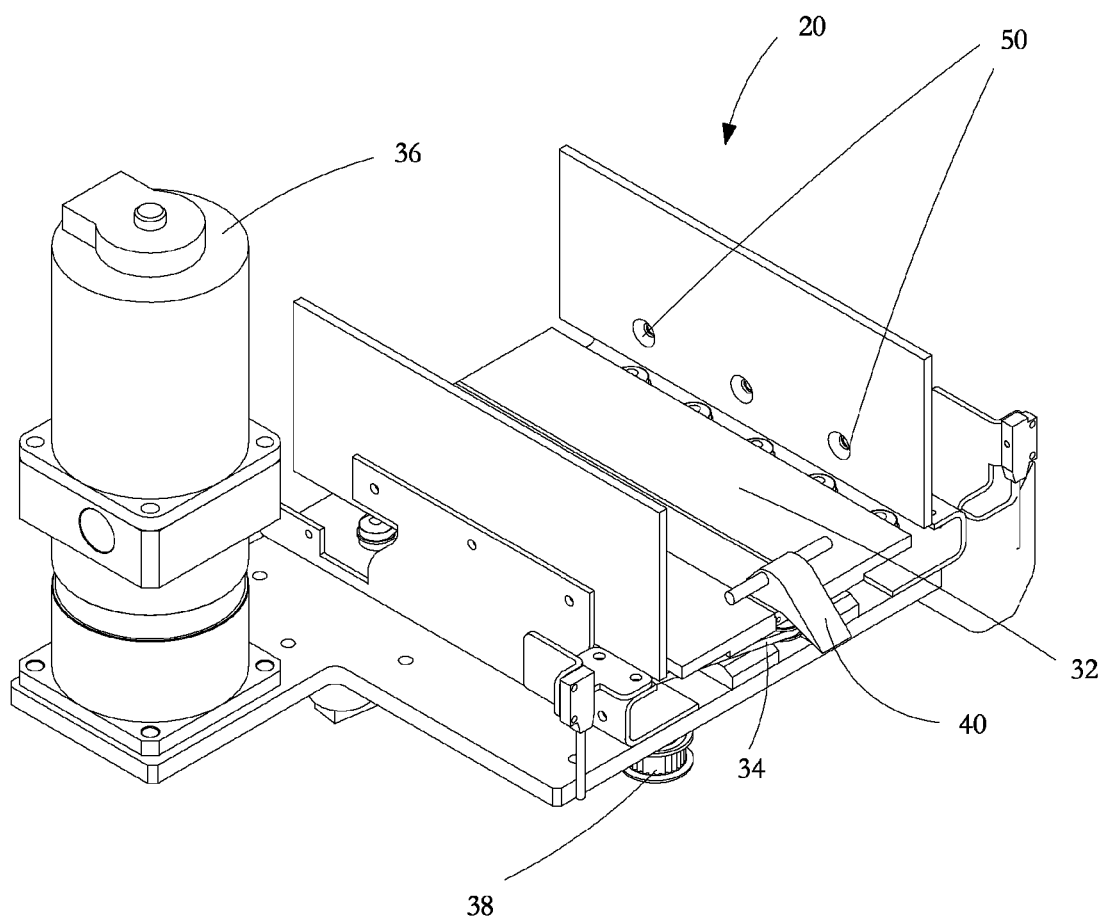
FIG. 2 is a perspective view of a pick head mechanism for use in an embodiment of the invention.

One form of pick head mechanism for use with the illustrated rack is described in U.S. patent application Ser. No. 12/503,989 which is hereby incorporated by reference in its entirety. As shown in the perspective view of FIG. 2, such a mechanism includes a telescopic supporting linkage 34 driven by a motor 36 and a belt 38 which are operable to drive a platform 32 supported on the linkage 34 into and out of the rack to pick or load a package at a selected bin. During a package picking procedure, the platform is driven into the selected bin where the package to be picked is caused to seat on the platform. The pick head mechanism is then actuated to withdraw the platform 32 from the selected bin or station and, at the same time, to drag the selected package onto the platform from where it is carried by the pick head 20 to another station within the dispensary. In a package place cycle, the package is initially supported on the platform 32. Then, as a result of the platform being driven into a chosen storage bin, the package is caused to dislodge and remain in the storage bin as the platform is withdrawn. The pick head mechanism is used to pick/place a selected package from/to a selected one of the stations/bins. If the selected package is part of a stack or row of packages, the pick head also picks/loads the package from/to a selected position within the stack or row.

It is important for patient convenience and safety that handling of medicament packages within the medicament vault be effected efficiently and securely in the course of various package handling procedures such as initial loading, subsequent inventory management, and dispensing. A valuable preparatory step for such handling is the serialization of all products that are stored at the dispensary.

Figure 3:
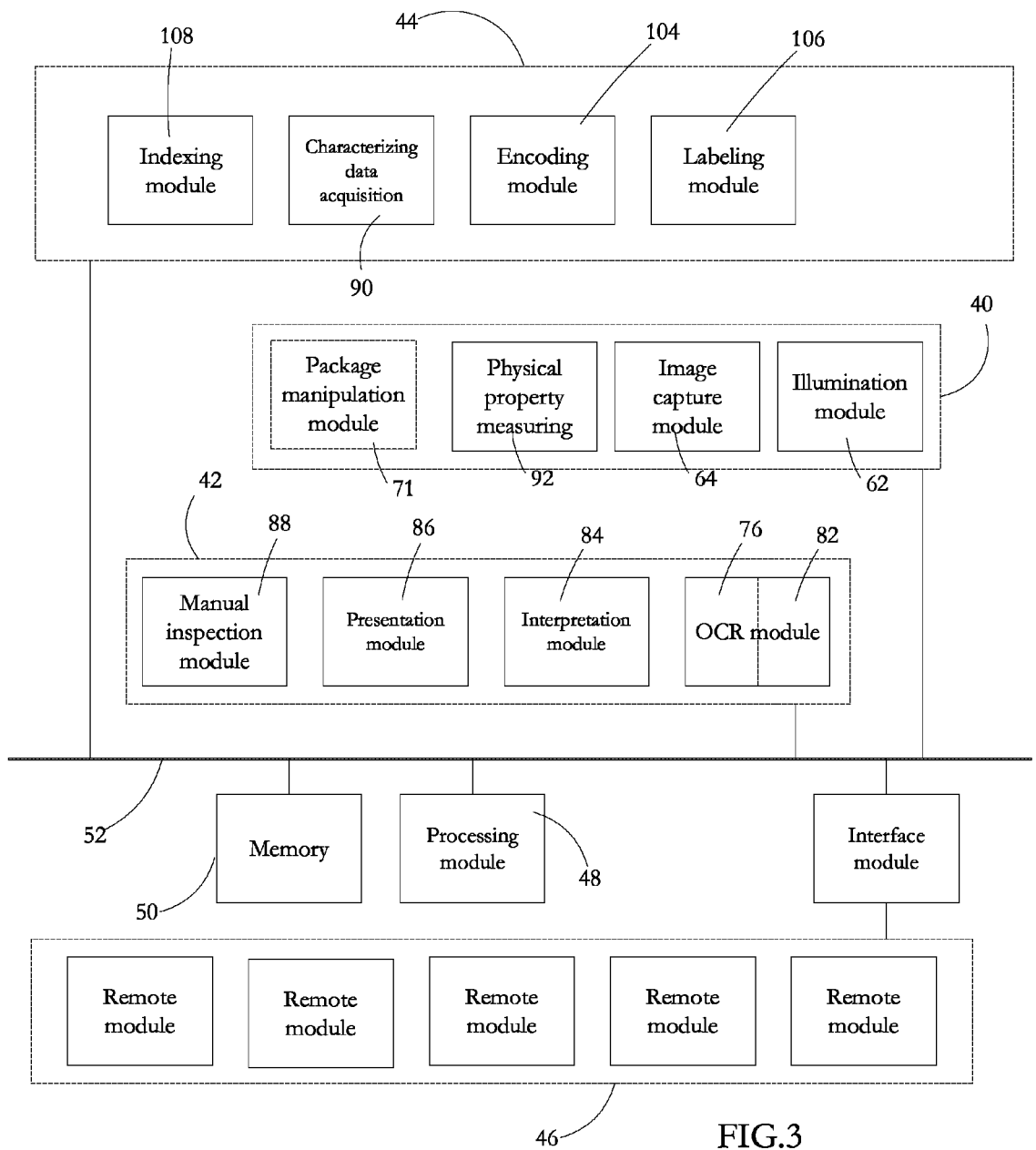
FIG. 3 is a circuit schematic diagram showing circuit modules used in handling a package for an automated dispensary according to an embodiment of the invention.

As shown in the schematic diagram of FIG. 3, the dispensary has an inspection module 40, an image processing module 42 and a serializing module 44. The dispensary modules are connected through an interface module to remote access modules 46 and other automated dispensaries forming a data communications network. Each of these general modules may include a number of sub-modules. The remote access modules 46 may for example include data input and output means for a doctor, a pharmacist, an inventory control network, and databases for drug data, patient drug history and patient medical history.

Package handling control is provided by a general processing module 48, a memory module 50 storing program instructions and other data to be used in the package handling control, and a connection bus 52. The processing module 48 may be a single processing device or a plurality of processing devices. Such a processing device may be a microcontroller, microprocessor, microcomputer, central processing unit, digital signal processor, programmable gate array, state machine, logic circuitry, and/or any device that manipulates signals (analog and/or digital) based on operational instructions. The memory module 50 may be a single memory device or a plurality of memory devices. Such a memory device may be a read-only memory, random access memory, system memory, flash memory, magnetic tape memory, programmable memory, erasable memory, and/or any device that stores digital information.

Figure 4:
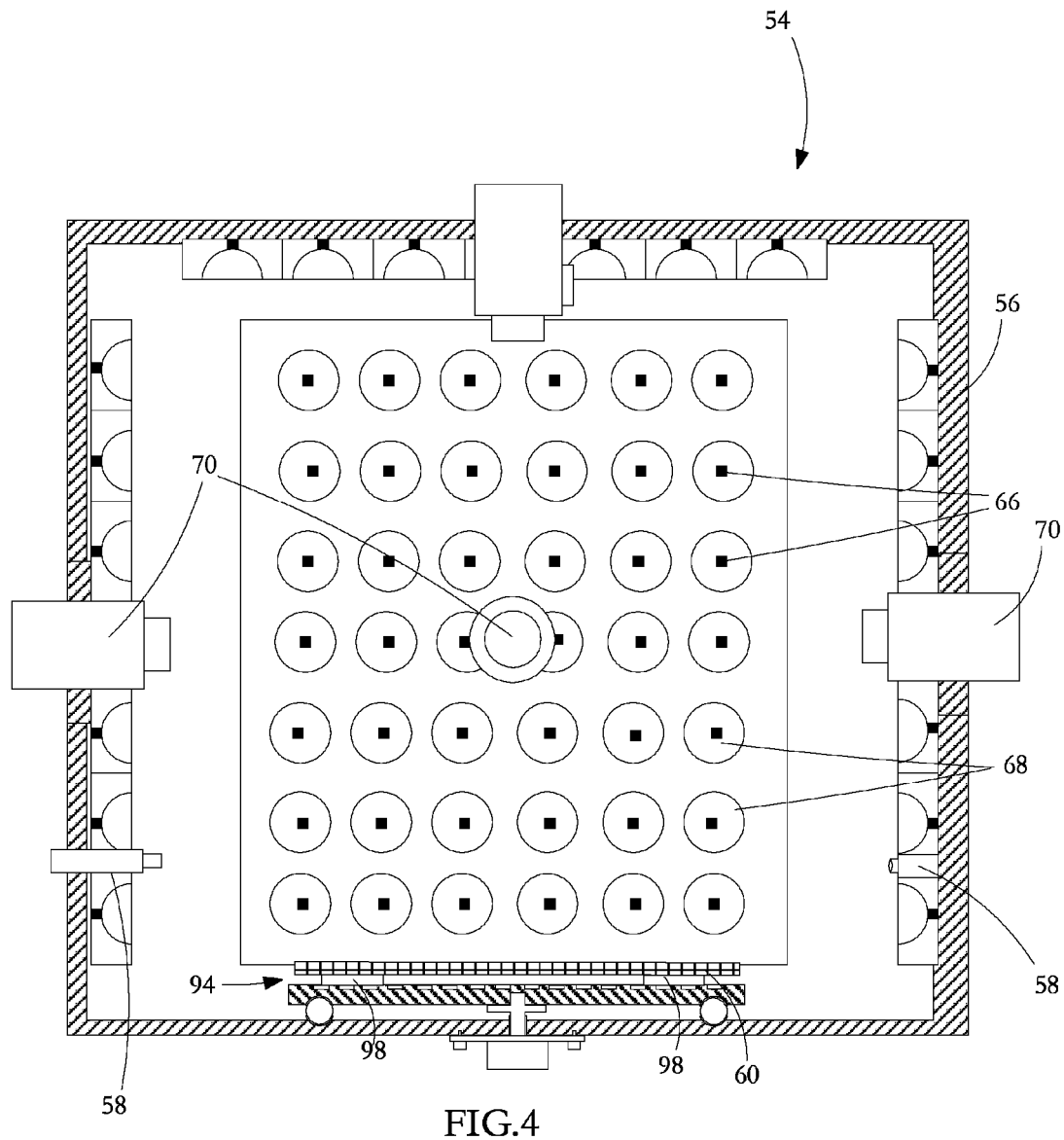
FIG. 4 shows a front view of an inspection station for an automated dispensary according to an embodiment of the invention.

Elements of the inspection module 40 are housed in an inspection station to which packages are brought and loaded for inspection in the course of serialization and at other times during their handling in the dispensary. As shown in FIG. 4, the inspection station includes a rectangular housing 54 having walls 56 in which are mounted optical sensors 58 that are triggered when the pick head 20 transfers a package into an inspection zone of the inspection station. Outputs from the optical sensors are used to generate command signals for manoeuvring the pick head so as accurately to place the package at a desired position on an inspection platform 60. Initial position and orientation of the package are selected to minimize subsequent processing requirements.

Constructed as part of the inspection station as shown in the circuit schematic diagram of FIG. 3 are an illumination module 62 and an image capture module 64. The illumination module has several light sources, which illuminate a package positioned at the inspection zone from multiple directions. Each source has an array of light emitting diodes (LEDs) 66 with light from each LED being focused by a respective lens 68 onto a corresponding surface of the package. The package is illuminated from above, and from top, bottom and both sides. In addition, for detecting and analyzing embossed characters, the package may be illuminated by other LED array sources (not shown) that direct light at a low angle to the package surfaces.

The image capture module includes cameras 70 mounted at positions where they capture an image from respective illuminated surfaces of the package when located at the inspection zone. The illumination and image capture modules are programmed to cycle through operation cycles so as to capture an image of each surface of the package. Packages are ideally placed into the inspection station at a location and with an orientation where, for a rectangular package and for reading printed characters from the package surfaces, each surface extends in a plane generally perpendicular to the direction of illuminating light and also generally perpendicularly to the viewing axis of a respective camera. In the FIG. 4 embodiment, the package (not shown) is maintained in a fixed position on the platform 60, while an illumination and image capture sequence takes place to capture images from the surfaces of the package.

Figure 5:
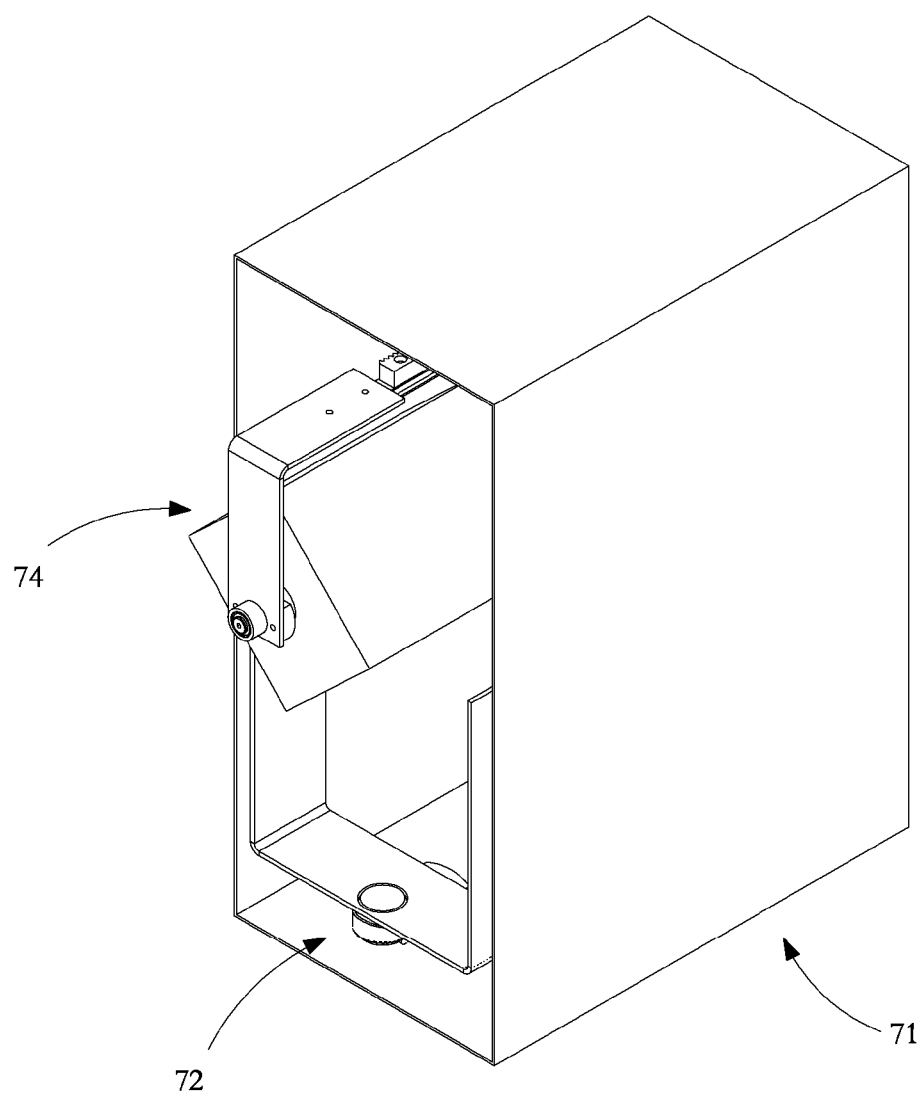
FIG. 5 shows a perspective view of part of another form of inspection station according to an embodiment of the invention.
Figure 6:
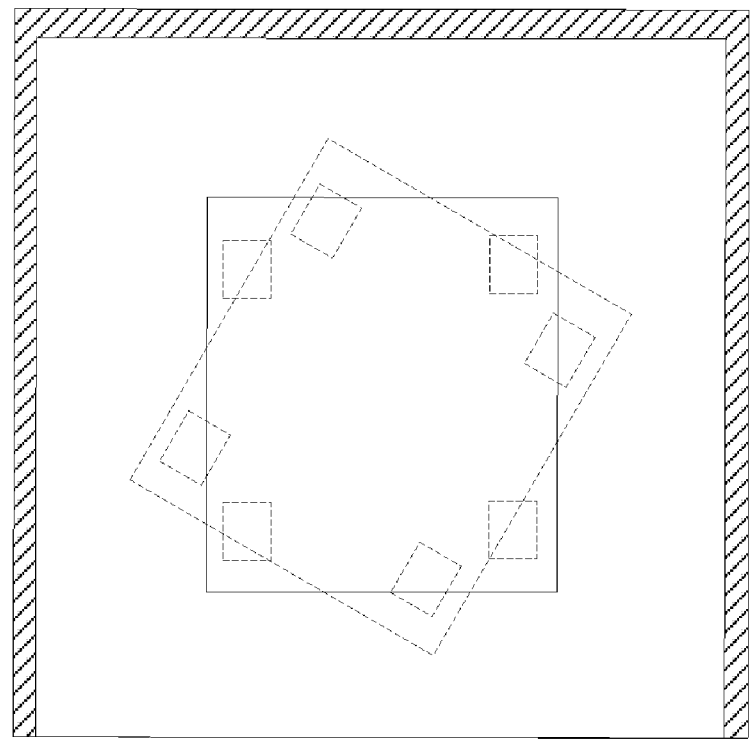
FIG. 6 is a plan view of part of the inspection station of FIG. 5.
Figure 7:
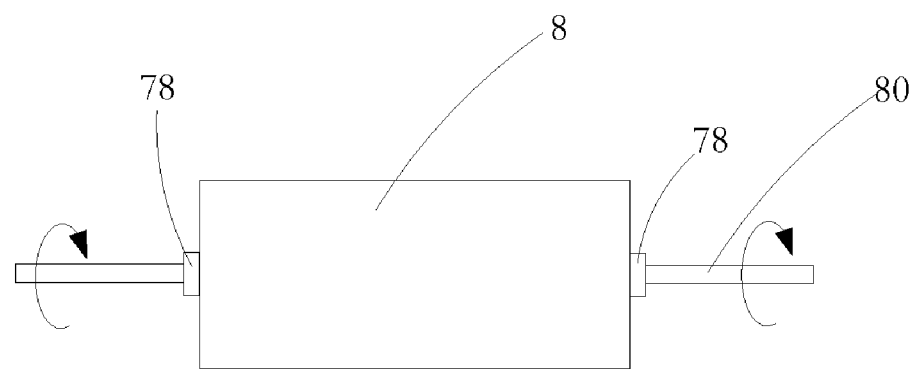
FIG. 7 is a side view of another part of the inspection station of FIG. 5.

In an alternative embodiment of the invention, an inspection station 54 includes a package manipulation module 71 as shown in FIG. 3 as part of the inspection module 40 and as shown in perspective view in FIG. 5. The package manipulation module 71 includes a first mechanism 72 for rotating a medicament package placed at an inspection zone around a vertical axis. During an inspection cycle, the medicament packages is supported on a base that is driven by a stepper motor to step the package through a series of orientations, one of which is shown in broken line in FIG. 6, showing a top view of the interior of the inspection station. Operation of the stepper motor is synchronized with operation of the light sources of the illumination module and operation of the cameras of the image capture module. The manipulation module has a second mechanism 74, part of which is shown in FIG. 7, for rotating the medicament package about a horizontal axis. The second mechanism includes a set of clamping pads 78 at the end of actuating rods 80, the rods being mounted for reciprocal movement along their longitudinal axes, and for rotation about their axes. During an inspection cycle, with a package 8 located at the inspection zone, the actuating rods 80 are caused to move against the package to grip it, are moved vertically to lift the package from the base, and are then caused to rotate about their longitudinal axes to spin the medicament package about a generally horizontal axis to bring top, bottom and two side surfaces successively before a light source of the illumination module. The operation of the second mechanism 74 is also synchronized with operation of the light sources 66 of the illumination module and operation of the cameras 70 of the image capture module. Parameters of the mechanisms 72, 74 are chosen to achieve the desired capture of images of the various surfaces of medicament packages placed at the inspection zone.

In a further modification of the manipulation module, the inspection station has a bay defined by three mutually perpendicular plates having an apex point. The pick head control is programmed to drive a package inserted into the inspection zone as far as possible into the bay towards the apex point with the package resting against the interior faces of the plates. The plates are transparent and cameras 70 are positioned on a side of respective plates remote from the bay interior. Each of the cameras has a field of view and depth of focus so as to span a predetermined area of the interior face of the corresponding plate. In this way, when a package is driven into position in the bay it is automatically at a position to obtain an image of each of its three 'contact" surfaces. Following imaging of the three faces, the package is gripped by an arrangement similar to that shown in FIGS. 5 and 7, and withdrawn from the bay. The package is turned 180° about one axis, then turned 180° about a perpendicular axis and finally driven back into the bay to the apex point whereupon images of the three other sides are captured. It will be appreciated that such a confined bay lends itself particularly to rectangular packages but is not as effective for packages with a round or irregular profile. In the latter, at the expense of a more complex mechanical arrangement, the plates may be dispensed with, the manipulation module then simply manipulating packages against virtual datum points or planes. Generally, by using a module such as the manipulation module 71, the illumination and image capture modules can be constructed with fewer elements because the package itself is moved to bring each of several surfaces to a position at which they are illuminated and at which a desired image or images of the illuminated surface is captured. However, as is evident, a more complex mechanical arrangement is required.

As shown in FIG. 3, an output from the inspection station representing the captured image is taken to the image processing module 42 which is operable to improve captured image quality and to identify characters. The image processing module includes an optical character recognition (OCR) module 76 optimized for reading printed machine-readable characters. The OCR module also includes an embossed character reader 82 for reading embossed characters often used for important package data such as lot number and expiry date. The embossed character reader can be as described in U.S. patent application Ser. No. 12/642,786 and can include dedicated illumination sources configured to project light at a low angle to the package surfaces to increase the ease of detecting and identifying the embossed characters.

The output from the OCR module 76 is fed to an interpretation module 84 interpretation which has a reference input from the serialization module 44 related to permitted and likely formats and content for characters and character sets that are expected to be read from the medicament package. These may include, for example, particular sequences of alphanumeric characters that normally signify a lot number or an expiry date; or the presence of separation spacing and characters between character strings of interest; or a particular format required by government regulations. The OCR output data is compared with the permitted and likely formats data to detect matches and so increase the confidence level of characters preliminarily identified at the OCR module. On the basis of a comparison between the OCR output and the expected data inputs at the interpretation module, OCR outputs are either confirmed as valid or are considered to be suspect.

Feedback control from the image processing module 42 is used for closed-loop analog tuning of the illumination module 62 and the image capture module 64. The feedback control may be configured as cascaded feedback with an output from one or more secondary feedback loop being used to reconfigure settings and with feedback from a primary loop being used to obtain a final output.

The output of the interpretation module 84 is taken to a presentation module 86 which is configured automatically to mark the image of the corresponding medicament package, as first captured by the image capture module 64, to highlight any character whose identity is in question. The output of the presentation module is transmitted to a manual inspection module 88 where a human inspector is present with access to monitor means the transmitted image is displayed for visual inspection by the inspector. The manual inspection module is located at a node on the communication network that is remote from the automated dispensary. For convenience, although the inspection module is at a remote node, it is shown in FIG. 3 as being part of the image processing module 42. The inspection module has input means at which the inspector can key in data to be sent on the network to be combined with other image data generated at the automated dispensary.

Output data from the image processing module 42 is recorded at a data acquisition module 90 forming part of the serialization module 44. The recorded data is source data and is visually discernable from the medicament package as delivered to the automated dispensary and includes both the images of the package and the characters that have been identified from those images. The source data forms one part of characterizing data corresponding to the medicament package.

In this embodiment of the invention, the characterizing data also includes derived data related to a physical property of the package, such as its weight. Such physical data may not be present in the source data and is not evident from a purely visual inspection of the medicament package as it is received from the manufacturer. The physical data is generated by measuring or otherwise inspecting physical properties of packages by the measuring module 92 located at the inspection station. As shown in FIG. 4, the physical property measuring module has a weigh scale sub-system 94. The weigh scale has four load cells 98 mounted between a base member 100 and the package-supporting platform 60, the load cells 98 being located in a symmetrical rectangular array. The load cells are compression load cells but can alternatively be tension or shear cells. They are constructed with the required sensitivity for the relatively light weight of conventional medicament packages. The cells incorporate strain gauge transducers but can alternatively incorporate other types of transducer. Components of the weight of the package are detected at each of the load cells and converted into corresponding output signals. Based on prior calibration, the weight of the package is computed. In addition, by comparing the variation in weight component measured by the load cells, moments of the package—i.e. the package weight distribution over the package length and breadth—are determined. While a rectangular array of load cells is a simple and convenient arrangement, a single load cell or an alternative array of load cells can alternatively be used.

It will be appreciated that other physical properties of the package such as its shape and size may also be measured by appropriate commercially available measuring units. Outputs from the physical property measuring module 92 are used to generate physical data corresponding to the measured physical properties, with the physical data forming a second data input to the data acquisition module 90. The combination of the source data and the physical data constitute the package characterizing data at the time that the package is serialized.

From the data acquisition module, an output is taken to an encoding module 104 for generating a code corresponding to the characterizing data. The code is used to generate a physical bar code which is applied to the surface of the corresponding package at a package labeling module 106.

The bar codes consolidate and compress the characterizing data for the serialized packages and have a consistent format, regardless of any significant distinction between the nature and properties of different packages.

The serializing module includes an indexing module 108 at which a first index is maintained of assigned bar codes against the corresponding characterizing data associated with the bar codes and a second index is maintained of the packages, as identified by their serializing bar codes, against the particular vault stations within which the packages are located at any time.

An autoserialization method using the above described equipment will now be described. Ideally, identifying data required for effective handling of medicament packages would be displayed on the packages and would have a standardized position, content and format. For example, all information would be printed black on white with all alphanumeric characteristics being of a single font type, stroke width, size and spacing. In fact, labeling of medicament packages from diverse commercial suppliers is not standardized to any great extent. Consequently, all incoming packages must be serialized as part of a standardized serialization procedure so that the incoming packages can subsequently be effectively handled within the dispensary.

In the present embodiment of the invention, packages are serialized in an autoserialization process in the course of a dispensary loading procedure, with the autoserialization process reusing a significant part of the result of labeling work done earlier in the supply chain. However, it will be realized that the autoserialization and loading processes for a particular medicament package can be performed at separate times.

Certain of the bins 12 in the vault are designated as loading bins, meaning that when the vault is first being stocked, or subsequently restocked, new stock assigned to the dispensary is first loaded into the loading bins without any particular regard to the nature or initial location of each package of the new stock. Subsequently, the packages are loaded into other bins of the vault designated as storage bins. The loading procedure can be effected at a quiet time, either when dispensing demand is predicted to be low or when, by automated monitoring, it is determined that no dispensing or other inventory management operation is in progress. The particular bins designated as loading bins can be changed if desired to have the loading area occupy either a smaller or larger footprint so as to accommodate a smaller or larger amount of new stock.

When transferring a package of new stock from one of the loading bins to a designated storage bin, various of the FIG. 3 serializing modules are actuated to serialize the packages to be loaded. A package to be serialized is selected and the pick head drive is actuated to move the pick head to a loading bin and to pick up the selected package located in one of the loading bins. The selected package is then brought by the pick head to the inspection station and inserted by the pick head to a reference position. The pick head is controlled by a servomechanism linked to the optical sensor arrangement to ensure that the package is accurately positioned on the inspection platform 60.

An imaging sequence is then initiated at the illumination module. The LED light sources 66 are operated in turn to illuminate successive faces of the package. Certain of the light sources are positioned and configured to emit light which is generally perpendicular to the surface to be imaged with a view to obtaining an image showing conventionally printed characters. Other light sources are configured to direct low angle light onto the surface to be imaged with a view to obtaining an image showing embossed characters. Certain of the light sources used may be white light containing a broad spectrum of wavelengths. These can be supplemented by single colour light sources which can offer clearer images of specific printed background/foreground combinations. The operation of the cameras 70 in the image capture module 64 is synchronized with the operation of light sources of the illumination module with the illumination and image capture modules programmed to cycle through an operation cycle so as successively to capture images from respective illuminated surfaces of the package when located at the inspection zone.

An output from the inspection station representing the captured image is taken to the image processing module 42 where the image quality is improved and where characters in the image are identified. At the OCR module 76, printed machine-readable characters are read by the OCR reader unless the image is unclear. Another input from the inspection module is taken to the embossed character reader 82 which reads embossed package data such as lot number and expiry date.

The output from the OCR module 76 is fed to the interpretation module 84 where it is compared to the reference inputs based on permitted and likely formats and content of characters. By detecting matches and the level of confidence in character identifications that have been preliminarily made at the OCR module is increased. On the basis of a comparison between the OCR output and the expected data inputs at the interpretation module, OCR outputs are either confirmed as valid or are considered to be suspect.

The output of the interpretation module 84 is taken to the presentation module 86 where the corresponding medicament package image, as first captured by the image capture module 64, is automatically marked to highlight any character whose identity is in question. The marked image is then displayed at the manual inspection module 88 where the human inspector visually inspects each of the questionable characters; i.e. those where a threshold level of confidence in the machine reading has not been reached. The inspector after having identified the questionable characters from displayed source data, keys in the interpretation for subsequent transmission back to the automated dispensary to be combined with the image data that has previously been machine read at the dispensary. The machine reading of characters from a package at the dispensary and the manual inspection of corresponding images at the manual inspection station can take place effectively as a contemporaneous operation. Alternatively, manual inspection tasks can be queued at a database that is accessed at another time such that identification of characters applied to a package is a phased activity.

As previously indicated the image processing module 42 includes one or more feedback loops. Feedback for tuning control of the illumination and image capture conditions is implemented by obtaining a rapid succession of images, scoring the quality of the images in terms of accurately detecting the characters in the images, and tuning the imaging conditions optimally to maximize the scores. The score from the OCR module 76 is used in a primary feedback loop to the illumination and image capture modules 62, 64 respectively to control, for example, the intensity and direction of the light sources, and to control various camera settings. The score is used as an error factor in a succession of PID (Proportional-Integral-Derivative) calculations to improve the score, with an optimal score being used as the basis for selecting final input data to the OCR module. The OCR feedback is used in real time to improve the imaging score. In addition, feedback is also used to set initial illumination and imaging conditions for a package known to be of the same type as that of a previously analyzed package. The primary feedback loop is combined with one or more secondary feedback loops from one or more internal sub-systems of the OCR module so as to increase the speed at which the OCR module operates. One secondary feedback loop determines which cameras of the image capture module are to be operational. For example, if the package is a bottle which invariably has no information of interest on the top or the bottom, then illumination sources and cameras occupying positions adjacent the bottle top and bottom are not operated. By means of another secondary feedback loop, the image capture module is initially operated to detect any UPC (universal product code) bar code on the package as obtained from the supplier. The UPC bar code is read and corresponding information is accessed from a product database on the network. From a review of this information, the initial orientation of the package and the expected position of other data elements on the packages are predicted. That information is then used as initial feedback to modify the settings of the illumination and image capture modules with a view to subsequently obtaining rapid and clear capture of further relevant image data. Illumination conditions, such as light intensity and beam direction, and camera settings, such as brightness, contrast, exposure, gain, focus, color saturation, zoom, pan and image sharpness, are adjusted in response to the feedback signals to increase the clarity of the final images and, therefore, to increase the confidence that a character is properly identified.

The output from the image processing module 42 is taken to the serialization module 44 where characterizing data for the package is generated at the data acquisition module 90 and the characterizing data is encoded at the encoding module 104. The serialization module also includes the labeling module 106 for labeling the package with a bar code representing the characterizing data, and the indexing module 108 for updating both the bar code/package index and the package/station index.

As previously described, one part of the package characterizing data is source data which includes the nature of the medicament, the manufacturer, the lot number, the expiry date and prescribed handling instructions. Typically, much of this is derived from a label bearing a representation of the source data applied to the medicament package at a prior juncture in the supply chain; for example, by the manufacturer shortly before the medicament package exits the manufacturing facility.

As previously described, another part of the characterizing data is physical data related to the physical properties of the package such as its weight, shape, size and moment. Such physical data is normally not evident from a visual inspection of packages as received for dispensary loading. The physical data is therefore generated by measuring designated physical properties of the package (or otherwise automatically physically inspecting the medicament package) at the physical property measuring module after the packages are loaded into the loading bins but before they are assigned to particular storage bins. The source and physical data are combined as the characterizing data for that package at the data acquisition module.

The bar code label is placed, where possible, at a consistent location on all packages so as to render subsequent detection and reading of bar codes quicker than if the bar codes were placed at random locations. It will be appreciated that other forms of label, such as a radio frequency identification label, can be used to encode the characterizing data and can be applied to packages in a conventional manner depending on the nature of the label. In subsequent handling of the labeled package, the bar code is read and referenced against the bar code/package index.

Once the bar code label is applied to a package at the inspection station, the pick head 20 is actuated to transfer the package from the inspection station to a selected one of the storage bins 12 and to a selected position in a row or stack of packages in that storage bin.

To select a storage bin within which the package is to be placed, a selection is made from the package characterizing data of all factors that determine a permissible bin selection. Because the vault 10 has a range of bin sizes, one such factor is package size. Clearly, it is not possible to place the package in a bin which is too small. Also, it is an inefficient use of space to place the package in a bin that is much larger than the package. The characterizing data is also analyzed for other factors that determine the nature of an acceptable storage bin such as the bin shape or depth. Some bins may be maintained in a refrigerated zone to accommodate packaged medicaments whose characterizing data shows that they are required to be stored at cold temperatures.

Once a suitable bin is identified, the bin index stored at indexing module 108 is checked to determine whether the bin is already fully occupied. If the bin is full, then the processing continues to review the suitability and state of fullness of other suitable storage bins. When a match of package and storage bin is obtained, a command sequence is initiated to have the pick head 20 retrieve the package from the inspection station and transfer it into the chosen storage bin. As part of the sequence, the package/station index is updated.

While, generally, the physical actions described in operation of the automated dispensary take place at the dispensary, because the dispensary is one node on a communications network, all steps in the various procedures described which relate to data access, storage and processing can readily take place at remote nodes of the network.

It will be seen that it is convenient, in the interests of efficient use of space and minimizing necessary physical movements of mechanical systems in the dispensary, to perform the various operations such as illumination, image capture, physical property measuring, package labeling, etc., at a single station configured to enable the performance of each of the operations. However, it will be understood that, the some of the operations can be performed at one station while other operations are performed at another station. To this end, the multiple stations can be configured differently or can be substantially identical to permit parallel processing of the operations on different packages. There is no intention that the implementation of operations involved in each of the procedures described should all be confined to one station of the dispensary if it should be found to be convenient to distribute the steps between different stations.

Although the storage stations of the illustrated embodiments are shown as a XY array of bins, the storage stations can be otherwise implemented. For example, in another embodiment of the invention, the bins have floors/ceilings but do not have side walls. Instead, packages are accurately placed at station locations along floor panels extending over at least part of the width of the rack, each package being separated from a next adjacent package not by a wall, but by an indexed space.

Other variations and modifications will be apparent to those skilled in the art. The embodiments of the invention described and illustrated are not intended to be limiting. The principles of the invention contemplate many alternatives having advantages and properties evident in the exemplary embodiments.

What is claimed is:

1. A method comprising:
   loading a plurality of packages into respective storage stations inside an automated dispensary, wherein each said package has a plurality of substantially planar outside surfaces bearing printed characters thereon;
   and
   for each package loaded inside the automated dispensary:
   retrieving the package from the corresponding said storage station;
   moving the package to an inspection station inside the automated dispensary;
   rotating the package about one or more axes of the one or more said substantially planar outside surfaces such that each is generally perpendicular to:
   an illumination of light emitted by one of a plurality of respective light sources in the inspection station; and
   a viewing axis of one of a plurality of respective image capture cameras in the inspection station;
   capturing an image of each substantially planar outside surface of the package that is generally perpendicular to:
   the illumination of light emitted by one of a plurality of respective light sources in the inspection station; and
   the viewing axis of one of a plurality of respective image capture cameras in the inspection station;
   reading each said captured image to identify source data;
   encoding the source data to obtain first encoded data;
   applying the first encoded data as an identifying label to the package;
   retrieving the labeled package from the inspection station inside the automated dispensary; and
   moving the labeled package to one of the storage stations inside the automated dispensary.

2. The method as defined in claim 1, wherein the retrieving of one said labeled package from one said storage station inside the automated dispensary further comprises using the index of the serialization codes against the storage stations for the retrieving of one said labeled package from one said storage station inside the automated dispensary.

3. The method as defined in claim 2, wherein each said captured image of each substantially planar outside surface of the package includes character data, and the method further comprises reading the character data with an optical character recognition reader.

4. The method as defined in claim 1, wherein:
   the automated dispensary is a node on a communications network; and
   said reading each said captured image further comprises transmitting the captured image from the dispensary in a transmission addressed for delivery to a remote node on the network whereby the captured image can be manually read at the remote node to derive a manually viewed part of the source data.

5. The method as defined in claim 1 in which the identifying label is one of a bar code and a radio frequency identification label.

6. The method as defined in claim 1, further comprising:
   receiving a written request from a user of the automated dispensary;
   optically scanning the written request to receive an optical image of the written request;
   retrieving one said labeled package from one said storage station inside the automated dispensary, wherein information in the optical image of the written request corresponds to the first encoded data on the identifying label on the retrieved one said labeled package; and
   dispensing the retrieved one said labeled package to the user of the automated dispensary.

7. The method as defined in claim 6, wherein the encoded data is a serialization code, and the method further comprises storing an index of said serialization codes against corresponding source data.

8. The method as defined in claim 7, further comprising storing the index of the serialization codes against the storage stations.

9. The method as defined in claim 1,
   further comprising, for each said package in the inspection station:
   measuring a physical property of the package to derive physical data;
   encoding the physical data to obtain second encoded data; and
   applying the second encoded data to the identifying label.

10. The method as defined in claim 1, wherein:
    each said illumination of light emitted by one of a plurality of respective light sources in the inspection station is an illuminating subsystem; and
    the method further comprises:
    recording a provisional image of the package with each said recording sub-system; and
    prior to capturing the image of each substantially planar outside surface of the package:
    analyzing the provisional image quality; and
    adjusting at least one of the illuminating sub-system and the recording sub-system to increase the provisional image quality.

11. An apparatus comprising:
    a loader module operable to load a plurality of packages into respective storage stations inside an automated dispensary, wherein each said package has a plurality of substantially planar outside surfaces bearing printed characters thereon;
    and
    for each package loaded inside the automated dispensary:
    a mover module operable to:
    retrieve the package from the corresponding said storage station; and
    move the package to an inspection station inside the automated dispensary;
    an inspection module in the inspection station inside the automated dispensary operable to rotate the package about one or more axes of the one or more said substantially planar outside surfaces such that each is generally perpendicular to:
    an illumination of light emitted by one of a plurality of respective light sources in the inspection station; and
    a viewing axis of one of a plurality of respective image capture cameras in the inspection station;

an image capture module operable to capture an image of each substantially planar outside surface of the package that is generally perpendicular to:
the illumination of light emitted by one of a plurality of respective light sources in the inspection station; and
the viewing axis of one of a plurality of respective image capture cameras in the inspection station;
a reading module operable to read each said captured image to identify source data;
an encoding module operable to encode the source data to obtain first encoded data;
a labeling module operable to apply the first encoded data as an identifying label to the package;
a first retrieving module operable to retrieve the labeled package from the inspection station inside the automated dispensary; and
a second mover module operable to move the labeled package to one of the storage stations inside the automated dispensary.

12. The apparatus as defined in claim 11, further comprising:
a user request receiver module operable to receive a written request from a user of the automated dispensary;
a scanning module operable to optically scanning the written request to receive an optical image of the written request;
a matching module operable to match information in the optical image of the written request corresponding to the first encoded data on the identifying label on one said;
a second retrieving module operable to retrieve the matching said labeled package from one said storage station inside the automated dispensary; and
a dispensing module operable to dispensing the retrieved matching said labeled package to the user of the automated dispensary.

13. The apparatus as defined in claim 12, wherein the reading module is at least one of a printed character reader and an embossed character reader.

14. The apparatus as defined in claim 11, wherein:
the automated dispensary is a node on a communications network; and
the reading module is further operable to transmit each said captured image from the dispensary in a transmission addressed for delivery to a remote node on the network whereby the captured image can be manually read at the remote node to derive a manually viewed part of the source data.

15. The apparatus as defined in claim 11, wherein the labeling module is further operable to apply one of a bar code and a radio frequency identification label to the package.

16. The apparatus as defined in claim 11, wherein:
the illumination module has multiple light sources to illuminate the package from a plurality of directions; and
the image capture module has image capture sub-units to capture images of the package as viewed from a corresponding plurality of directions.

17. The apparatus as defined in claim 11, further comprising a physical property measuring module to measure at least one physical property of the package to derive physical data, wherein:
the encoding module is operable to encode the physical data to obtain second encoded data; and
the labeling module is operable to label the package with a label embodying the second encoded data.

18. The apparatus as defined in claim 11, wherein:
each said illumination of light emitted by one of a plurality of respective light sources in the inspection station is an illumination module;
the image capture module is further operable to capture a provisional image of the package;
the reading module is further operable to:
read the provisional image; and
develop a feedback signal;
and
the apparatus further comprises a feedback loop to apply the feedback signal to adjust settings of at least one of:
a corresponding said illumination module; and
the image capture module.

19. A method comprising:
loading a plurality of packages into respective storage stations inside an automated dispensary that is a node on a communications network, wherein each said package has a plurality of substantially planar outside surfaces bearing printed characters thereon;
for each package loaded inside the automated dispensary:
retrieving the package from the corresponding said storage station;
moving the package to an inspection station inside the automated dispensary;
rotating the package about one or more axes of the one or more said substantially planar outside surfaces such that each is generally perpendicular to:
an illumination of light emitted by one of a plurality of respective light sources in the inspection station, wherein each said illumination of light emitted by one of a plurality of respective light sources in the inspection station is an illuminating subsystem; and
a viewing axis of one of a plurality of respective image capture cameras in the inspection station;
recording a provisional image of the package with each said recording sub-system;
analyzing the provisional image quality;
adjusting at least one of the illuminating sub-system and the recording sub-system to increase the provisional image quality;
capturing, after said recording, analyzing and adjusting, an image of each substantially planar outside surface of the package that is generally perpendicular to:
the illumination of light emitted by one of a plurality of respective light sources in the inspection station; and
the viewing axis of one of a plurality of respective image capture cameras in the inspection station;
reading each said captured image to identify source data;
transmitting the captured image from the dispensary in a transmission addressed for delivery to a remote node on the network, whereby the captured image can be manually read at the remote node to derive a manually viewed part of the source data;
encoding the source data to obtain first encoded data
measuring a physical property of the package to derive physical data;
encoding the physical data to obtain second encoded data;
applying the first and second encoded data as an identifying label to the package;
retrieving the labeled package from the inspection station inside the automated dispensary;
moving the labeled package to one of the storage stations inside the automated dispensary;

receiving a written request from a user of the automated dispensary;

optically scanning the written request to receive an optical image of the written request;

retrieving one said labeled package from one said storage station inside the automated dispensary, wherein information in the optical image of the written request corresponds to the first encoded data on the identifying label on the retrieved one said labeled package; and dispensing the retrieved one said labeled package to the user of the automated dispensary.

* * * * *